US008785167B2

(12) United States Patent
Potember et al.

(10) Patent No.: US 8,785,167 B2
(45) Date of Patent: Jul. 22, 2014

(54) BIOCOMPATIBLE ARTICLE FOR THE TREATMENT OF WATER AND PRODUCTION OF ENERGY

(75) Inventors: Richard S. Potember, Dayton, MD (US); Jennifer L. Breidenich, Atlanta, GA (US); Julia B. Patrone, Laurel, MD (US)

(73) Assignee: The Johns Hopkins University, Baltimore, MD (US)

( * ) Notice: Subject to any disclaimer, the term of this patent is extended or adjusted under 35 U.S.C. 154(b) by 398 days.

(21) Appl. No.: 13/116,617

(22) Filed: May 26, 2011

(65) Prior Publication Data

US 2011/0294159 A1 Dec. 1, 2011

Related U.S. Application Data

(60) Provisional application No. 61/348,776, filed on May 27, 2010.

(51) Int. Cl.
| | | |
|---|---|---|
| C12N 11/02 | (2006.01) | |
| C12N 11/10 | (2006.01) | |
| C12N 11/08 | (2006.01) | |
| C02F 3/10 | (2006.01) | |
| C12N 11/06 | (2006.01) | |

(52) U.S. Cl.
CPC .............. *C12N 11/08* (2013.01); *C12N 11/10* (2013.01); *C02F 3/108* (2013.01); *C12N 11/06* (2013.01)
USPC .......................................... 435/177; 435/41

(58) Field of Classification Search
CPC ........ C02F 3/102; C12N 11/02; C12N 11/04; C12N 11/06; C12N 11/08; C12N 11/10; C12N 11/12
See application file for complete search history.

(56) References Cited

U.S. PATENT DOCUMENTS

| | | | |
|---|---|---|---|
| 5,308,704 | A | 5/1994 | Suzuki et al. |
| 5,795,480 | A | 8/1998 | Keun et al. |
| 6,265,203 | B1 | 7/2001 | Ushiyama |
| 6,395,521 | B1 | 5/2002 | Miura |
| 6,673,447 | B2 | 1/2004 | Wei et al. |
| 6,887,692 | B2 | 5/2005 | Paterek |
| 6,893,567 | B1 | 5/2005 | Vanotti et al. |
| 7,029,884 | B2 | 4/2006 | Maekawa |
| 7,223,327 | B2 | 5/2007 | Schlenoff et al. |

(Continued)

FOREIGN PATENT DOCUMENTS

| | | |
|---|---|---|
| CN | 1789414 | 7/2001 |
| JP | 1043184 | 2/1989 |

(Continued)

OTHER PUBLICATIONS

Ratliff et al., Attachment of mycobacteria to fibronectin-coated surfaces, 1988, Journal of General Microbiology 134(5): 1307-1313.*

(Continued)

*Primary Examiner* — Jon P Weber
*Assistant Examiner* — Robert Yamasaki
(74) *Attorney, Agent, or Firm* — Noah J. Hayward

(57) ABSTRACT

A biocompatible article including (a) a biocompatible hydrogel; (b) an adhesive coating on at least a portion of the hydrogel; and (c) one or more organisms adhered to at least a portion of the adhesive coating is disclosed.

21 Claims, 3 Drawing Sheets

(56) References Cited

U.S. PATENT DOCUMENTS

| | | |
|---|---|---|
| 7,737,240 B2 | 6/2010 | Marks et al. |
| 7,745,023 B2 | 6/2010 | Flickinger et al. |
| 2003/0175824 A1* | 9/2003 | Pishko et al. .................. 435/7.2 |
| 2010/0159539 A1 | 6/2010 | Ascon et al. |

FOREIGN PATENT DOCUMENTS

| | | |
|---|---|---|
| JP | 1228471 | 9/1989 |
| JP | 10109097 | 4/1998 |
| JP | 10180277 | 7/1998 |

OTHER PUBLICATIONS

Nuttelman et al., Attachment of fibronectin to poly (vinyl alcohol) hydrogels promotes NIH3T3 cell adhesion, proliferation, and migration, 2001, Journal of Biomedical Materials Research 57(2): 217-223.*

* cited by examiner

BIOCOMPATIBLE ARTICLE FOR THE TREATMENT OF WATER AND PRODUCTION OF ENERGY

CROSS-REFERENCE TO RELATED APPLICATIONS

This application claims the benefit of prior filed co-pending U.S. Provisional Application No. 61/348,776, filed May 27, 2010, the contents of which are incorporated by reference herein.

BACKGROUND OF THE INVENTION

1. Field of the Invention

The present invention generally relates to a biocompatible article for the treatment of water and production of energy such as hydrogen or hydrocarbons.

2. Description of the Related Art

There are many types of water treatment systems, such as filtration and cleaning systems for treatment of water in, for example, swimming pools and aquariums. Many of these systems filter the water to remove suspended matter and reduce the cloudy appearance of the water. Preventing bacterial growth in water and removing contaminants from water are significant industrial, as well as household, problems. For example, industrial effluent should be cleaned to remove toxic compounds as well as to remove bacteria before it is dumped into lakes and rivers. Containers of water such as swimming pools, hot tubs, aquariums and the like must be kept clean to prevent the water from becoming cloudy and/or the container walls from becoming slimy. The water may be treated by active means such as a filter to remove particles and bacteria, and it may also be treated by passive means whereby a biocide is placed in a container and floated in the water.

It is common to use chemical means to keep the water clean and reduce growth of bacteria and other microorganisms. Ultraviolet light, chlorination, bromination, treatment with ions of copper and silver as well as treatment with ozone can be used to treat and/or disinfect water. These are typical biocides, that is, substances or energies that destroy living organisms. Of course care must be taken with all these methods because of the possible toxicity or damage to the user. Chemicals require careful handling to avoid environmental contamination as well as contact with the user.

In addition, global warming has been a main factor that causes abnormal weather worldwide and breaks the global ecosystem, so that prevention of global warming is a worldwide issue that should be addressed urgently. It has turned out that global warming is caused mainly by a large consumption of fossil fuel including oil and coal and the resulting warming gases such as carbon dioxide ($CO_2$). Accordingly, there is a strong demand for research in new technologies for suppressing the release of global warming gases, creation of energy sources, such as hydrogen, utilizing biofunctions, and study of immobilization and degradation of global warming gases.

Among these, bio energy or fuel energy is advantageous in that it can be converted to electrical energy with high efficiency in the form of a fuel cell, the amount of the generated heat is 3 or 4 times that generated by oil, only water is generated after combustion so that there is no fear of environmental pollution, and that water, which is the raw material for hydrogen energy, is abundant.

CN1789414 A discloses a method for different biomass raw materials to ferment and produce hydrogen using a continuous, highly effective and stable microbial source. CN1789414 A further discloses that the method employs a polyvinyl alcohol glue solution, bacterial flora liquid (dehydrogenase enzymatic activity i¦50 U/mL) comprising the single bacterial flora liquid and miscegenation bacterial flora liquid, 8-16% alta-mud (adsorbing carrier), and an auxiliary agent: 10-20% $CaCO_3$, 0.1-0.2% sulfo-aminolactic acid or cysteine, sulphate cation M(M=$Fe^{2+}$, $Ni^{2+}$, $Fe^{3+}$, $Mg^{2+}$, $K^+$, $Mn^{2+}$), ammonium salt anion N(N=$[Mo_7O_{24}]^{6-}$, $[C_2O_4]^{2-}$, $[C_6H_5O_7]^{3-}$, $SO_4^{2-}$), and 1% $Na_2S$. The method disclosed in CN1789414 A uses the sugar S(S=xylo-pfan, lactose, grape-sugar, cane sugar, amylogen, potato) and fresh potato hydrolysate as raw material to continuously ferment and produce hydrogen.

Accordingly, there is a continued need for improved systems that can treat water and produce energy such as hydrogen in a simple, cost efficient manner.

SUMMARY OF THE INVENTION

In accordance with one embodiment of the present invention, there is provided a biocompatible article comprising (a) a biocompatible hydrogel; (b) an adhesive coating on at least a portion of the hydrogel; and (c) one or more organisms adhered to at least a portion of the adhesive coating.

In accordance with a second embodiment of the present invention, there is provided a process for preparing a biocompatible article comprising (a) providing a biocompatible hydrogel; (b) applying an adhesive coating on at least a portion of the hydrogel; and (c) adhering one or more organisms to at least a portion of the adhesive coating.

In accordance with a third embodiment of the present invention, there is provided a method for the production of energy comprising (a) providing a biocompatible article comprising (i) a biocompatible hydrogel; (ii) an adhesive coating on at least a portion of the hydrogel; and (iii) one or more organisms adhered to at least a portion of the adhesive coating; and (b) exposing the biocompatible article to one or more environmental conditions sufficient to allow the organisms to produce a measurable amount of energy.

In accordance with a fourth embodiment of the present invention, there is provided a method for the treatment of water comprising (a) providing a biocompatible article comprising (i) a biocompatible hydrogel; (ii) an adhesive coating on at least a portion of the hydrogel; and (iii) one or more organisms adhered to at least a portion of the adhesive coating; and (b) contacting the biocompatible article with a water source containing a sufficient amount of impurities for a suitable time to reduce the amount of impurities therein.

The biocompatible articles of the present invention are flexible, lightweight hydrogels that are capable of acting as a self-contained bioreactor for bio-energy applications. For example, the biocompatible articles are particularly suitable for treating water and for the production of energy such as conversion of solar energy to hydrogen or hydrocarbons. In addition, the biocompatible articles can be rolled-up in a dehydrated state thereby rendering them portable. Accordingly, upon reaching a desired location for use, the portable, rolled-up articles can be rehydrated and re-used for the treatment of water and/or energy production, i.e., as a lightweight power source.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows.

DETAILED DESCRIPTION OF PREFERRED EMBODIMENT(S)

Figure 1:
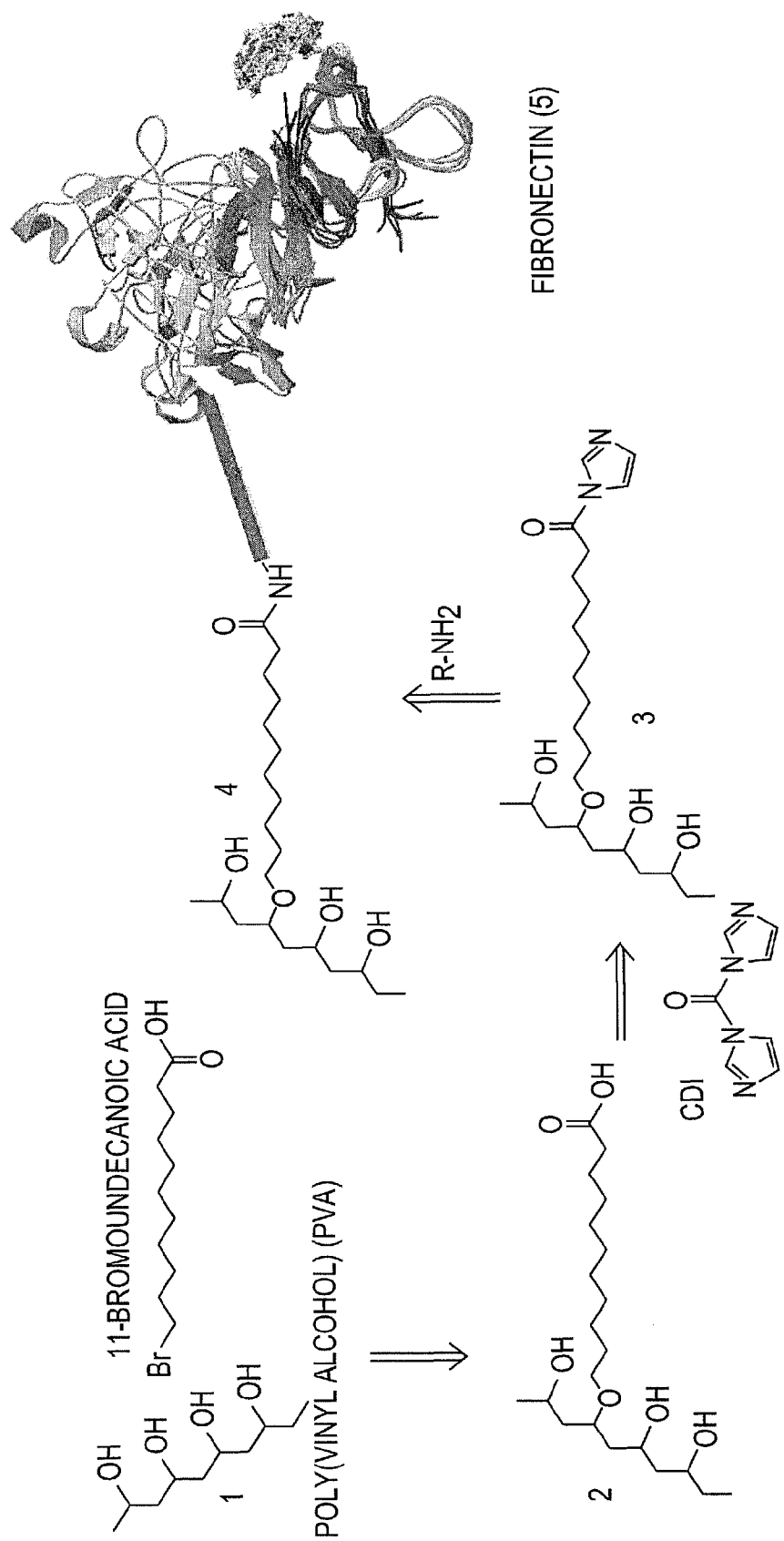
FIG. 1 is a schematic flow chart illustrating a synthesis procedure for attaching an adhesive coating to the surface of the biocompatible hydrogel according to one embodiment of the present invention.

One aspect of the present invention is directed to a biocompatible article for the treatment of water and/or the production of energy such as hydrogen or hydrocarbons. In general, a biocompatible article of the present invention includes (a) a biocompatible hydrogel; (b) an adhesive coating on at least a portion of the hydrogel; and (c) one or more organisms adhered to at least a portion of the adhesive coating.

Biocompatible hydrogels in general are a well-known class of materials and include 3-dimensional, water swollen polymer networks that are made insoluble by cross-links. These crosslinks can be either chemical or physical in nature and determine the polymer structural characteristics. Accordingly, the hydrogels comprise hydrated, cross-linked polymeric systems containing water in an equilibrium state. The hydrogels for use herein generally have a water content greater than about 5 weight percent and more commonly between about 10 to about 80 weight percent.

The biocompatible hydrogels can be any material known in the art capable of forming a biocompatible article according to the present invention. In one embodiment, the biocompatible hydrogels are formed from materials which include, by way of example, polyhydroxyethyl acrylate, polyhydroxyethyl methacrylate, polyvinyl pyrrolidone (PVP), polyacrylic acid, polymethacrylic acid, polyacrylamide, polydimethylacrylamide (DMA), polyvinyl alcohol and the like and copolymers thereof, e.g., from two or more monomers selected from hydroxyethyl acrylate, hydroxyethyl methacrylate, N-vinyl pyrrolidone, acrylic acid, methacrylic acid, acrylamide, dimethyl acrylamide, vinyl alcohol and the like. Alternatively, the biocompatible hydrogel can include naturally-occurring materials such as hyaluronic acid, polysaccharides, such as cross-linked carboxyl-containing polysaccharides, agarose, dextran, carrageenan, alginic acid, starch, cellulose, or derivatives of these such as, for example, carboxymethyl derivatives, chitan, chitosan and the like and combinations thereof. The nature of the materials employed to form the biocompatible porous matrix should be selected so the formed biocompatible hydrogels have sufficient porosity to allow for the flow of water and other small molecules such as micronutrients, e.g., cobalt, copper, zinc, and nickel; nitrates; nitriles, carbohydrates and the like through the hydrogel. The biocompatible hydrogels are commercially available, or can be obtained by methods well known in the art.

In one preferred embodiment, a suitable biocompatible hydrogel is derived from chitin, chitosan and mixtures thereof. Chitin is a natural fiber extracted from the shells of crustaceans such as shrimp, crab and lobster. Chitosan is the most common derivative of chitin. In general, to prepare chitin, the ground shellfish exoskeletons are decalcified with dilute acid, deproteinated with dilute alkali and the resulting material is bleached or decolorized. By treating the chitin with hot concentrated alkali, some or all of the N-acetyl groups may be removed resulting in a modified carbohydrate, polyglucosamine or chitosan. It is a non-toxic, biocompatible and biodegradable natural polymer. It is a member of a class of biopolymers called hydrocolloids, but has atypical properties. While most hydrocolloids are neutral or negatively charged at biological pH values, chitosan is positively charged. Its cationic nature in acid solution is ideal, as the positively charged chitosan is attracted to negatively charged surfaces.

In one preferred embodiment, a suitable biocompatible hydrogel is obtained from poly(vinyl alcohol) (PVA). For example, PVA hydrogels can be obtained by a method which requires the use of a chemical solvent such as glyocal, gluteraldehyde, or borate to chemically crosslink linear polymer chains. As with any material intended for environmental uses, it is desirable to minimize the amount of residual solvents present in the resulting hydrogel. An alternative solvent-free method for creating crosslinked PVA hydrogels is through the use of a freeze-thawing technique. This technique creates crystalline areas within the PVA which act as sites for semi-permanent physical crosslinks. There are a variety of parameters that can be altered to affect the structural characteristics of the PVA hydrogels via the freeze-thawing technique. These include the molecular weight of the PVA, the polymer solution concentration, the number of freeze-thaw cycles, the temperature extremes the polymer is exposed to, and the length of time of both the freezing and thawing steps.

Covalently cross-linked PVA hydrogels can be produced by making a physically associated PVA hydrogel that has a crystalline phase, forming covalent crosslinks by exposing the physically associated PVA hydrogel to an effective amount of ionizing radiation, and removing the physical associations by exposure to a temperature above the melting point of the physically associated crystalline phase to produce a covalently cross-linked vinyl polymer hydrogel. The physical properties of the produced hydrogel can be adjusted by varying controlled parameters such as the proportion of physical associations, the concentration of polymer and the amount of radiation applied. PVA covalently cross-linked vinyl polymer hydrogels can be made translucent, preferably transparent, or opaque depending on the processing conditions. The stability of the physical properties of the produced hydrogel can be enhanced by controlling the amount of covalent crosslinks.

Such PVA hydrogels can be made to have a wide range of mechanical properties, such as very low to moderately high compressive moduli. Critical to the final modulus is the number of physical associations present in the precursor gels. A large number of physical associations serve to reduce the total yield of the radiation induced crosslinks, reducing the final modulus of the material. Thus, weakly associated precursor physical gels produce stronger covalently cross-linked vinyl polymer hydrogels. This phenomenon allows control of the final material properties by modulation of the physical associations in the precursor gel.

The porosity and pore size in covalently cross-linked vinyl polymer hydrogels can be controlled in that the melt-out step removes physical associations, leaving voids of controllable volume.

PVAs are commonly divided into "fully hydrolyzed" and "partly hydrolyzed" types, depending on how many mole-percent of residual acetate groups remain in the molecule. PVAs can be manufactured from polyvinyl acetate by alcoholysis using a continuous process. By varying the degree of polymerization of the polyvinyl acetate and its degree of hydrolysis (saponification) a number of different grades can be supplied. Typically, suitable polyvinyl alcohols for the practice of the present invention have a degree of hydrolysis (saponification) of about 80 to about 100 percent.

Crosslinks in PVA hydrogels may be either covalent (chemical) crosslinks or physical associations (physical). Covalent crosslinks are formed typically through chemical modification, or through irradiation. Physical associations may be formed, for example, via freeze-thaw cycling, dehydration or by a combination of such methods. For example, both covalent and physical associations can be employed, in that a physically cross-linked precursor gel will be covalently crosslinked by irradiation.

The use of irradiation to form covalent crosslinks has several advantages over chemical crosslinking. Chemical crosslinking is often performed by the addition of a reactive metallic salt or aldehyde and subjecting the system to thermal radiation. For example, crosslinking may be performed by adding (di-) isocyanates, urea-/phenolic-melamine-resins, epoxies, or (poly-) aldehydes. However, the use of such reagents for chemical crosslinking can leave residues that decrease the biocompatibility of the PVA hydrogel.

In general, the resulting biocompatible hydrogel will have a thickness ranging from about 500 nanometer to about 100 millimeters.

As one skilled in the art will readily appreciate, the biocompatible hydrogel can have surface reactive functional groups that are inherently present at the surface of the device. However, if the biocompatible hydrogel contains too few or no functional groups, the surface of the device can be modified by known techniques, for example, plasma chemical methods (see, for example, WO 94/06485), or conventional functionalization with groups such as —OH, —NH$_2$ or —CO$_2$H. Suitable surface reactive functional groups of the biocompatible hydrogel include a wide variety of groups well known to the skilled artisan. Representative examples of such reactive functional groups include, but are not limited to, hydroxy groups, amino groups, carboxy groups, carbonyl groups, aldehyde groups, sulfonic acid groups, sulfonyl chloride groups, isocyanato groups, carboxy anhydride groups, lactone groups, azlactone groups, epoxy groups and groups being replaceable by amino or hydroxy groups, such as halo groups, or mixtures thereof. In one embodiment, the surface reactive functional groups of the biocompatible hydrogel are carboxy groups, amino groups and/or hydroxy groups.

An adhesive coating is then applied on at least a portion of the surface of the biocompatible hydrogel. In one embodiment, the adhesive coating is formed from a bio-adhesive agent such as, for example, fibronectin, laminin, collagen, vitronectin, polypeptides and the like and any combination thereof. In this embodiment, it may be necessary to use a coupling agent bound between the external surface of the biocompatible hydrogel and the adhesive coating in order to attach the adhesive coating to at least a portion of the surface of the hydrogel. As discussed above, a biocompatible hydrogel will comprise a polymeric material having reactive functionalities at the surface thereof such as hydroxyl groups, carboxylic acid groups, amine groups, etc. Accordingly, the point of attachment of the polymeric material with the coupling agent is through the result of the reaction of complementary reactive functionalities of the coupling agent with the reactive functionalities on the surface of the biocompatible hydrogel.

Figure 2:
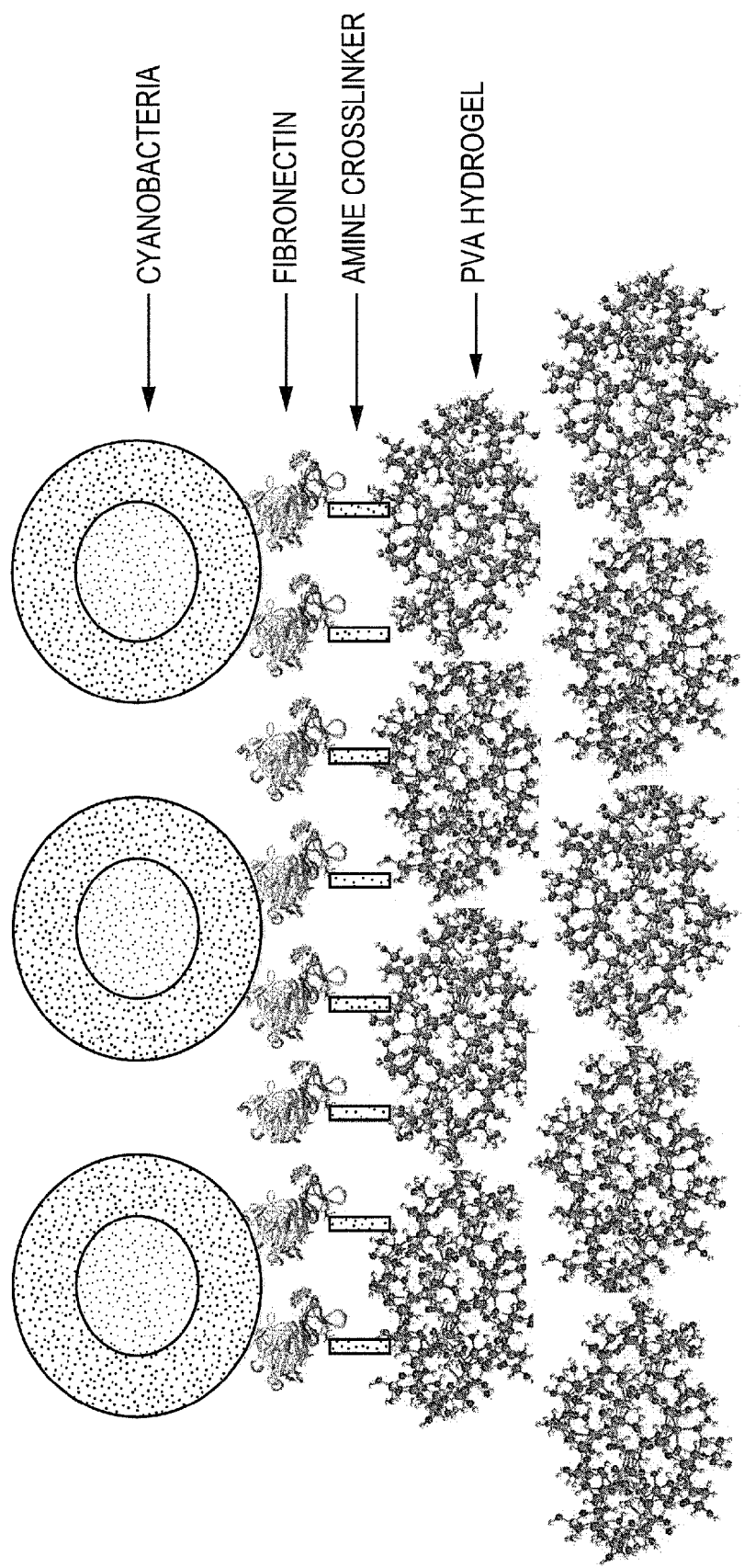
FIG. 2 illustrates a biocompatible article according to one embodiment of the present invention.

As one skilled in the art will readily appreciate, in the case of a PVA hydrogel which has hydroxyl surface reactive functional groups, it may be necessary to modify one or more of the hydroxyl to be able to attach the adhesive coating thereto. For example, as shown in FIG. 1, a PVA hydrogel (1) containing one or more hydroxyl surface reactive functional groups can first be reacted with a bromoalkanoic acid such as 11-bromoundecanoic acid to convert the one or more hydroxyl groups to an acid group of compound (2). Next, compound (2) is then reacted with a suitable coupling reagent such as carbonyl diimidazole (CDI) to convert the acid group to a highly reactive N-acylimidazole of compound (3), which is then reacted with an amine group of the formula R—NH$_2$, wherein R is a C$_1$-C$_{20}$ hydrocarbyl group such as to provide an activated acid group of compound (4). Finally, the one or more reactive functionalities found on fibronectin, e.g., an amine group, are reacted with the activated acid group to provide a stable link between fibronectin and the polymer chain (see also FIG. 2).

In another embodiment, the adhesive coating is attached by way of at least one polyelectrolyte layer of an oppositely-charged polymer onto the surface of the hydrogel without involving any chemical reaction. Polyelectrolytes, by virtue of available cationic or anionic functionalities in abundance, provide an excellent means to glue molecular components. Cooperativity and electrostatic interactions, hydrogen bonding, and/or Van der Waals interaction between anionic and cationic sites leads to the formation of strong association of multilayers.

Figure 3:
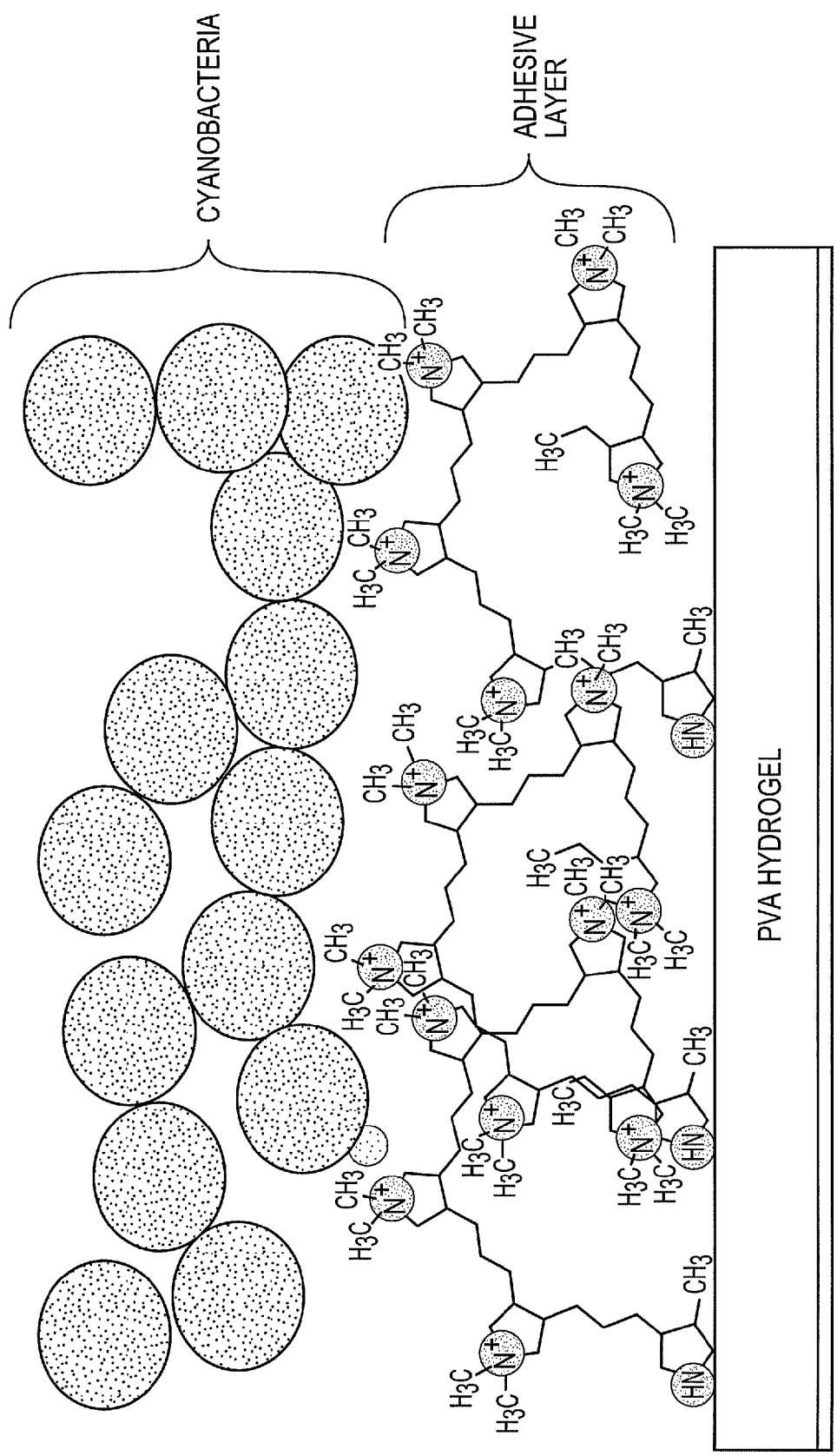
FIG. 3 illustrates a biocompatible article according to another embodiment of the present invention.

Examples of polyelectrolytes that can be used include commercially available polyelectrolytes, branched or linear polyethyleneimine (PEI), polyacrylic acid (PAA), polymethacrylic acid (PMA), polystyrene sulfonate (PSS), polydiallyl dimethyl ammonium chloride (PDDA), polyvinylpyridine (PVP), polyvinyl sulfate (PVS), polyallylamine hydrochloride (PAH), their chemically altered derivatives, and any combination thereof. In one embodiment, the at least one polyelectrolyte layer is formed from a positively charged polyelectrolyte layer such as a PDDA$^+$ layer (see also FIG. 3). In another embodiment, the hydrogel can be coated with multiple polyelectrolyte layers. For example, the hydrogel can contain a positively charged polyelectrolyte layer such as a PDDA$^+$ layer; then a negatively charged layer such as a PSS$^-$ layer and then another positively charged polyelectrolyte layer such as a PDDA$^+$ layer.

In general, the surface of the hydrogel is therefore chemically tuned through a composition of the polyelectrolyte deposition solution. For example, in neutral or basic solution where the pH is greater than the isoelectric point of hydrogel, the hydrogel surface is negatively charged and readily adsorbs positively charged polyelectrolytes. Accordingly, one could bind a polyelectrolyte such as PDDA, which remains an anionic species even in highly acidic solution (e.g., a pH about.1), to recreate a positively charged surface suitable for deposition of the organism.

The deposition method may be variable. For example, a simple dip coating procedure involving immersion of the hydrogel to be treated in the appropriate polyelectrolyte of enzyme solutions. However, spray coating or spin coating methods, which are readily amenable for commercial applications, can also be used to fabricate the catalytic multilayers on the hydrogel.

Once the adhesive coating is attached to the surface of the hydrogel, one or more organisms are adhered to at least a portion of the adhesive layer. A suitable organism includes any organism capable of producing energy such as hydrogen or hydrocarbons. Representative examples of such organisms includes cells of algae, microalgae, funghi, cyanobacteria or other bacteria having a photosynthetic photosynthesis system, plant cell cultures or plant homogenate, selected mutants, or genetically modified organisms. In one preferred embodiment, the organism is cyanobacteria. Useful cyanobacteria includes, by way of example, *Synechococcus* species of cyanobacteria or a *Synechocystis* species of cyanobacteria.

The organisms are adhered to the adhesive coating by way of electrostatic attraction as discussed above. For example, in the case of cyanobacteria, cyanobacteria possesses a negative charge and therefore will adhere to the positive charge of either fibronectin or the positive charge of the top layer of the polyelectrolyte layer.

The resulting biocompatible article is portable, in that the hydrogel can be dehydrated and roll-up for easy transportation to a desired location of use. The dehydrated hydrogel can be rehydrated and then re-used. The resulting biocompatible article is particularly useful in treating water and for the production of energy such as hydrogen or hydrocarbons. In one embodiment, a method for the production of energy includes (a) providing a biocompatible article comprising (i) a biocompatible hydrogel; (ii) an adhesive coating on at least a portion of the hydrogel; and (iii) one or more organisms adhered to at least a portion of the adhesive coating; and (b) exposing the biocompatible article to one or more environmental conditions sufficient to allow the organisms to produce a measurable amount of energy. In general, suitable environmental conditions include light, temperature, nutrients, salinity, pH and the like. As one skilled in the art will readily appreciate, the appropriate environmental condition will necessarily depend upon the specific organism being used to produce the measurable amount of energy. A suitable light source includes a light source such as solar light to produce the energy upon exposure to the organisms. In use, the biocompatible article is placed in a photobioreactor and exposed to, for example, the light source for a suitable time until a sufficient amount of energy is generated from the organisms. The energy such as hydrogen or hydrocarbons can then be used, for example in a fuel cell for the generation of electricity.

In accordance with another embodiment of the present invention, a method for the treatment of water includes (a) providing a biocompatible article comprising (i) a biocompatible hydrogel; (ii) an adhesive coating on at least a portion of the hydrogel; and (iii) one or more organisms adhered to at least a portion of the adhesive coating; and (b) contacting the biocompatible article with a water source containing a sufficient amount of impurities for a suitable time to reduce the amount of impurities therein. In general, the water can be retention ponds, estuary ponds and the like. Typically, the water in need of treatment will contain one or more impurities such as, for example, organic waste products containing nitrogen compounds. In use, one or more of the biocompatible articles of the present invention is placed in the water for a time period sufficient to allow the water to flow through the article thereby removing the impurities. In addition, by being exposed to the water, the organisms such as cyanobacteria will continue to grow and create a network on the surface of the article.

The following examples are provided to enable one skilled in the art to practice the invention and are merely illustrative of the invention. The examples should not be read as limiting the scope of the invention as defined in the claims.

EXAMPLE 1

Step I—Preparation of Hydrogel

A 20% by weight PVA solution was prepared by adding 4 g PVA (MW-22,000 by weight) to an Erlenmeyer flask to 16 mL of deionized water (DI) water. The solution was heated to 80° C. and stirred for approximately 10 minutes. The solution was then allowed to cool to room temperature and 3 mL of the PVA solution was placed in a scintillation vial. A 25% by wt. solution of gluteraldehyde was then added to the PVA solution to get a final concentration of 1 wt. %. Next, 10 drops of 2M HCl was added to the scintillation vial. Since gelation should occur quickly, the solution was immediately transferred to a glass slide and covered with an additional glass slide. The glass sides were placed in a vacuum desiccators and allowed to gel.

Step II—Coating Procedure—Fibronectin Coating

The hydrogel of Step I was covalently coated with fibronectin using the method disclosed in Nuttleman, et al., "Attachment of fibronectin to poly(vinyl alcohol) hydrogels promotes NIH3T3 cell adhesion, proliferation, and migration", John Wiley & Sons, Inc. pp. 217-223 (2001), the contents of which are incorporated by reference herein. First, the hydrogel of Step I was added to 10 mL of 3.0 M NaOH in a 20 mL scintillation vial. Next 100 g of 1'-bromoundecanoic acid (11-BUDA, Aldrich) was added to the vial and the vial was stirred at 37° C. for 2 hours. The hydrogel was rinsed several times with water to remove unreacted 11-BUDA and reaction byproducts. The hydrogel was then placed in a vacuum oven overnight to dry completely.

Acetone (10 mL) and carbonyl diimidazole (CDI, Aldrich) were added to the hydrogel in a scintillation vial, and the CDI was allowed to react with the pendant acid groups for 2 hours at room temperature. The hydrogel was then rinsed several times with acetone, allowed to dry, and sterilized under ultraviolet light in a sterile hood for several hours. A sterile fibronectin solution (50 mg/mL in 0.1 M sodium carbonate buffer, pH 9-10) was prepared and added to the hydrogel disks in a 10 mL conical tube. This coupling reaction of the fibronectin to the PVA hydrogel occurred at room temperature for 2 hours.

The hydrogel was washed three times with 1× phosphate-buffered saline (PBS) and stored overnight at 4° C. The hydrogel was washed in 70% isopropanol and stained using primary and secondary antibodies to allow fluorescent visualization of the fibronectin coating.

Step III—Attachment of Organisms to Hydrogel

A 500 ml of cyanobacteria liquid culture was added to the coated hydrogel of Step II and incubated at room temperature, with light, in a BG-11 media ($NaHCO_3$, HEPES, distilled $H_2O$). The cyanobacteria were allowed to grow over a period of several days to weeks and images were taken periodically to record growth.

EXAMPLE 2

Step I—Preparation of Hydrogel

A 20% by weight PVA solution was prepared by adding 4 g PVA (MW-22,000 by weight) to an Erlenmeyer flask to 16 mL of deionized water (DI) water. The solution was heated to 80° C. and stirred for approximately 10 minutes. The solution was then allowed to cool to room temperature and 3 mL of the PVA solution was placed in a scintillation vial. A 25% by wt. solution of gluteraldehyde was then added to the PVA solution to get a final concentration of 1 wt. %. Next, 10 drops of 2M HCl was added to the scintillation vial. Since gelation should occur quickly, the solution was immediately transferred to a glass slide and covered with an additional glass slide. The glass sides were placed in a vacuum desiccators and allowed to gel.

Step II—Coating Procedure—Polyelectrolyte Coating

First, a 2% $PDDA^+$ and a 2% $PSS^-$ solution were separately prepared in 0.1 M NaCl. The hydrogel of Step I was allowed to soak in the $PDDA^+$ solution for five minutes, dipped into 0.1 M NaCl, and rinsed in distilled water. The $PDDA^+$ coated hydrogel was allowed to air dry (or nitrogen gas can be used) to blow off excess liquid. Next, the $PDDA^+$ coated hydrogel was allowed to soak in the PSS⁻ solution for five minutes, dipped into 0.1 M NaCl, and rinsed in distilled water. The PDDA⁺/PSS⁻ coated hydrogel was allowed to air dry (or nitrogen gas can be used) to blow off excess liquid. The PDDA⁺/PSS⁻ coated hydrogel was allowed to soak again in the PDDA⁺ solution for five minutes, dipped into 0.1 M NaCl, and rinsed in distilled water. The coated hydrogel was allowed to air dry (or nitrogen gas can be used) to blow off excess liquid. The resulting hydrogel was then soaked in a PBS buffer until it was exposed to the bacteria in Step III.

Step III—Attachment of Organisms to Hydrogel

A 500 ml of cyanobacteria liquid culture was added to the coated hydrogel of Step II and incubated at room temperature, with light, in a BG-11 media ($NaHCO_3$, HEPES, distilled $H_2O$). The cyanobacteria were allowed to grow over a period of several days to weeks and images were taken periodically to record growth.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A biocompatible article, comprising: (a) a biocompatible hydrogel; (b) an adhesive coating on at least a portion of the hydrogel; and (c) one or more organisms comprising cyanobacteria adhered to at least a portion of the adhesive coating.

2. The biocompatible article of claim 1, wherein the biocompatible hydrogel comprises poly(vinyl alcohol).

3. The biocompatible article of claim 1, wherein the biocompatible hydrogel comprises a polymer derived from chitin or chitosan.

4. The biocompatible article of claim 1, wherein the adhesive coating is derived from a bio-adhesive agent.

5. The biocompatible article of claim 4, wherein the bio-adhesive agent comprises fibronectin.

6. The biocompatible article of claim 4, wherein the adhesive coating is attached to the hydrogel through a coupling agent which is bound to an outer surface of the hydrogel and to the bio-adhesive agent.

7. The biocompatible article of claim 1, wherein the adhesive coating comprises at least one polyelectrolyte layer.

8. The biocompatible article of claim 7, wherein the at least one polyelectrolyte layer possesses a positive charge.

9. The biocompatible article of claim 1, wherein the one or more organisms comprising cyanobacteria comprise a *Synechococcus* species of cyanobacteria or a *Synechocystis* species of cyanobacteria.

10. The biocompatible article of claim 1, wherein the biocompatible article can be rolled-up in a dehydrated state.

11. A biocompatible article, comprising: (a) a biocompatible hydrogel comprising poly(vinyl alcohol); (b) an adhesive coating comprising fibronectin on at least a portion of the hydrogel; and (c) one or more organisms comprising cyanobacteria adhered to at least a portion of the adhesive coating.

12. A process for preparing a biocompatible article, the process comprising (a) providing a biocompatible hydrogel; (b) applying an adhesive coating to at least a portion of the hydrogel; and (c) adhering one or more organisms comprising cyanobacteria to at least a portion of the adhesive coating.

13. The process of claim 12, wherein the biocompatible hydrogel comprises a poly(vinyl alcohol) hydrogel.

14. The process of claim 13, wherein the adhesive coating comprises fibronectin having one or more reactive functionalities and the organism is cyanobacteria.

15. The process of claim 14, wherein the step of applying the adhesive coating to at least a portion of the hydrogel comprises (i) converting one or more hydroxyl groups of the poly(vinyl alcohol) hydrogel to one or more carboxylic acid groups; (ii) converting the one or more carboxylic acid groups to one or more N-acylimidazole groups; (iii) converting the one or more N-acylimidazole groups to one or more activated acid groups; and (iv) attaching the one or more reactive functionalities of the fibronectin to the activated acid groups of the poly(vinyl alcohol) hydrogel.

16. The process of claim 15, comprising (i) reacting a bromoalkanoic acid with the one or more hydroxyl groups of the poly(vinyl alcohol) hydrogel to provide one or more carboxylic acid groups; (ii) reacting carbonyl diimidazole with the one or more carboxylic acid groups to provide one or more N-acylimidazole groups; (iii) reacting an amine group of the formula R-NH2 wherein R is a C1-C20 hydrocarbon group with the one or more N-acylimidazole groups to provide one or more activated acid groups; and (iv) reacting the one or more reactive functionalities of the fibronectin to the activated acid groups of the poly(vinyl alcohol) hydrogel.

17. The process of claim 12, wherein the biocompatible hydrogel comprises a polymer derived from chitin or chitosan.

18. The process of claim 12, wherein the step of applying the adhesive coating to at least a portion of the hydrogel comprises applying a polyelectrolyte layer to at least a portion of the hydrogel, wherein the polyelectrolyte layer possesses a positive charge.

19. The process of claim 18, wherein the polyelectrolyte layer is polydiallyl dimethyl ammonium chloride (PDDA+).

20. A method for the production of energy comprising (a) providing a biocompatible article comprising (i) a biocompatible hydrogel; (ii) an adhesive coating on at least a portion of the hydrogel; and (iii) one or more organisms comprising cyanobacteria adhered to at least a portion of the adhesive coating; and (b) exposing the biocompatible article to one or more environmental conditions sufficient to allow the organisms to produce a measurable amount of energy.

21. A method for the treatment of water comprising (a) providing a biocompatible article comprising (i) a biocompatible hydrogel; (ii) an adhesive coating on at least a portion of the hydrogel; and (iii) one or more organisms comprising cyanobacteria adhered to at least a portion of the adhesive coating; and (b) contacting the biocompatible article with a water source containing a sufficient amount of impurities for a suitable time to reduce the amount of impurities therein.

* * * * *